United States Patent [19]

Brunhouse

[11] Patent Number: 4,490,473
[45] Date of Patent: Dec. 25, 1984

[54] LABELED ANTIBODIES AND METHODS

[75] Inventor: Robert F. Brunhouse, San Jose, Calif.

[73] Assignee: PanAb, Santa Clara, Calif.

[21] Appl. No.: 479,789

[22] Filed: Mar. 28, 1983

[51] Int. Cl.³ .................... G01N 33/54; G01N 33/58
[52] U.S. Cl. .................................. 436/518; 436/531;
   436/543; 436/544; 436/545; 436/546; 436/547;
   436/815; 436/822; 260/112 R; 260/112 B;
   564/284; 564/287; 564/289; 424/85; 424/88
[58] Field of Search .................... 564/284, 287, 289;
   260/112 R, 112 B; 436/518, 531, 543–547, 815,
   822; 424/85, 88

[56] References Cited
PUBLICATIONS

Prange, et al., J. of Immunology, vol. 118, #4, (1977), pp. 1311–1316.
Alevy et al., J. Immunology, vol. 124, #1, (1980), pp. 215–221.
Alevy et al., J. Exp. Med., vol. 151, (1980), pp. 528–541.

*Primary Examiner*—Christine M. Nucker
*Attorney, Agent, or Firm*—William B. Walker

[57] ABSTRACT

Sandwich immunoassays are provided wherein an anti-analyte antibody is coupled with a detector labeled antibody, the anti-analyte antibody being substituted with a N,N,N-trimethylammoniumphenyl group and the detector labeled antibody is an antibody specific to the N,N,N-trimethylammoniumphenyl group. The invention includes novel assays, antigens and antibodies.

11 Claims, No Drawings

LABELED ANTIBODIES AND METHODS

FIELD OF THE INVENTION

This invention relates to immunoassay methods having improved sensitivity, to novel reagents therefore, and to novel intermediates and methods for manufacturing the reagents. In particular, this invention relates to improved reagents useful in sandwich immunoassays.

BACKGROUND OF THE INVENTION

There is a continually expanding need to determine the presence of minute quantities of organic materials in aqueous solutions and to quantify their concentrations. Concentrations of interest range from about $10^{-4}$ to $10^{-12}$M or even lower. Areas where the determinations are most significant include detecting the presence of drugs of abuse in physiological media, metering of therapeutic dosages of drugs, diagnosis of disease where the presence, absence or amount of a particular organic material is relevant to the diagnosis, and in assays for trace contaminants of food. Non-physiological areas of interest include investigations of water contamination, quality control, and the like. Despite major advances in the immunoassay field, the precise determination of low concentrations of organic compounds continue to present problems, and many important compounds still cannot be routinely detected or measured.

Sandwich immunoassays were developed to provide increased sensitivity. In these procedures, an antibody which selectively binds to an analyte is provided with a hapten label. A second antibody, which selectively binds with the hapten label, is provided. The second antibody is provided with a detector label, e.g. a radioactive element, fluorescent substituent, enzyme, or the like which can be used to quantify the amount of detector labeled conjugate. Applying hapten labels to antibodies presents a number of special problems. Antibody solubility is reduced when bound to previously used haptens. Since most assays are carried out in aqueous medium, this insolubility presents a limiting aspect of hapten labeling. Furthermore, many haptens reduce antibody activity when coupled to the antibody.

DESCRIPTION OF THE PRIOR ART

Hapten-sandwich labeling has been described by S. Cammisuli et al in "Hapten-sandwich labeling", *The Journal of Immunology*, 117,(5) pp 1695-1704 (1976) and in U.S. Pat. Nos. 4,185,084 and 4,230,683. U.S. Pat. No. 4,243,749 is directed to a competition sandwich immunoassay employing an enzyme label.

Homogeneous immunoassays relying on competition between an analyte and an analyte analogue labeled with a fluorescent material or a fluorescent quencher are described in U.S. Pat. Nos. 3,998,943, 4,261,968 and 4,256,834. In these assays, the fluorescent compound is a hapten, and a quencher for the hapten can comprise an antibody to the fluorescent compound. M. Lamm et al in "Hapten-Conjugated Antibodies and Visual Markers Used to Label Cell-Surface Antigens for Electron Microscopy: An Approach to Double Labeling", *Proc. Nat. Acad. Sci. U.S.A.*, 69,(12) pp 3732-3736 (1972) have described procedures to locate antigens of cell surfaces employing two bridging techniques. In the hybrid antibody bridge method, a hapten is coupled to a specific antibody which is then allowed to bind to cells. The cell-bound antibodies are, in turn, bridged to visual markers by hybrid F(ab')2-fragments, of which one valence is directed to the hapten and the other valence to the marker. In the second method, an untreated antihapten antibody bridge method, the hapten is coupled to both the specific antibody and the visual marker.

D. Pressman et al in *J. Amer. Chem. Soc.* 68, pp 250-255 (1946) describe the reactions of antiserum to the p-azophenyltrimethylammonium group. Antibodies were prepared by innoculating rabbits with the reaction product of diazotized trimethyl-(p-aminophenyl)-ammonium chloride hydrochloride and ovalbumin. This azo compound reacts with the tyrosyl and histidyl units of ovalbumin, coupling directly with the aromatic ring of the tyrosyl group, and the azo compound severely decreases solubility of the proteins coupled therewith. L. Piette et al in *Immunochemistry*, 9, pp 17-22 (1972) describes the study of spin-labeled phenyltrimethylammonium substituted compounds which have been immobilized by rabbit antibodies to p-azophenyltrimethylammonium groups. Coupling p-azophenyltrimethylammonium with succinylated bovine serum albumin and isolation of rabbit serum antibodies thereto is described by Fenton et al in *Biochemistry*, 10 (8), pp 1429-1437 (1971).

Protein conjugates of 4-fluoro-3-nitrophenyltrimethylammonium iodide with amino acids and with bovine insulin have been described by D. Sutton et al in *Biochem. J.* 130, pp 589-595 (1972), and in *Hoppe-Seyler's Journal Z. Physiol. Chem.* 357, pp 971-976 (1976). Similarly, B. Easter et al in *Hoppe-Seyler's Z. Physiol. Chem.* 360, pp 1335-1342 (1979) have described crystalline derivatives of bovine insulin reacted with this compound. C. Bevan et al in *J. Chem. Soc.* (*B*), pp 238-241 (1968) describe the study of reaction rates of methoxide ion with 3-fluoro-5-nitrophenyltrimethylammonium chloride.

SUMMARY OF THE INVENTION

An immunological assay for determining antibody of the formula:

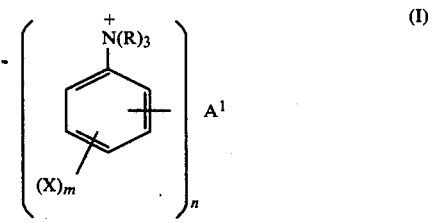

wherein $A^1$ is an antibody bonded through an amino linkage thereof;

R is methyl or ethyl;

X is nitro, iodo, bromo, methoxy, carboxy or acetyl;

m is 0, 1 or 2; and n is from 1 to 350.

comprising conjugating therewith detector labeled antibody prepared in immunological response to antigenic compound having the formula:

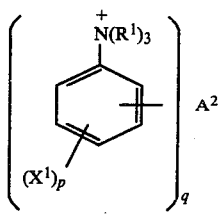

wherein $A^2$ is an antigen bonded through an amino linkage thereof, and $A^2$ is preferably not the same as $A^1$;

$R^1$ is methyl or ethyl;

$X^1$ is nitro, iodo, bromo, methoxy, carboxy or acetyl;

p is 0, 1 or 2; and q is from 1 to 350.

The novel antibodies, antigenic compounds and methods for their preparation which are used in the above assay are further aspects of this invention.

DETAILED DESCRIPTION OF THE INVENTION

In sandwich immunoassays applications employing a first hapten conjugated antibody and a second anti-hapten antibody, the first antibody is allowed to conjugate with the analyte ligand. The ligand-antibody complex is then separated from the unbound first antibody. The second antibody is then used to detect the presence of the first. The ligand-antibody complex is brought together with the second antibody which binds to the first antibody by means of the hapten. Second antibodies may be labeled with suitable detection labels such as radioactive materials, fluorochromes, or enzymes, for example. Alternatively, the binding of second antibody may be inferred by the adherence of the complex to a solid surface to which this second antibody is adherent or by the ability of the complex to activate the complement components in sera, or by other means known in the art.

In competitive assays, such as are described in U.S. Pat. Nos. 4,243,749 and 4,185,084, the analyte analogue labeled with a detector label and a first antibody to the analyte are mixed with analyte solution. Addition of a second antibody specific to the first antibody forms insoluble complexes which can be separated. Detector label can be measured in the remaining solution or separated complex and correlated to controls to indicate the original analyte concentration.

A key aspect of these immunoassays as practiced according to this invention comprises an assay for determining N,N,N-trimethylammoniumphenyl conjugated antibody of the formula:

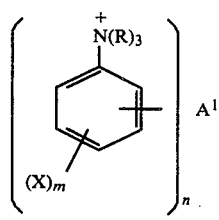

wherein $A^1$ is an antibody and $A^1$ is bonded through an amino linkage of the antibody;

R is methyl or ethyl;

X is nitro, iodo, bromo, carboxy or acetyl;

m is 0, 1 or 2; and n is from 1 to 350.

comprising conjugating therewith a labeled antibody composition prepared in immunological response to N,N,N-trimethylammoniumphenyl conjugates of the formula:

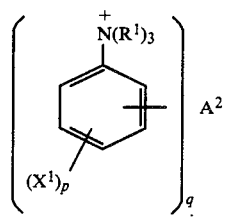

wherein $A^2$ is an antigen bonded through an amino linkage, and $A^2$ is preferably not the same as $A^1$;

$R^1$ is methyl or ethyl;

$X^1$ is nitro, iodo, bromo, methoxy, carboxy or acetyl;

p is 0, 1 or 2; and q is from 1 to 350.

The antibody $A^1$ of Formula I is a first antibody reagent which conjugates to form an antibody-antigen complex with an analyte to be determined or measured. The antibody $A^1$ is therefore prepared to specifically conjugate with the target analyte according to procedures which are well known in the art. In general, the target analyte, when innoculated into a suitable animal species, effects an immunological response, generating antibodies which will specifically conjugate with the analyte. If the analyte is a non-antigenic hapten, the analyte species can be coupled to an antigenic protein prior to innoculation. Procedures for preparing antibodies to selected analytes are described by A. Voller et al in *Immunoassays for the 80's*, University Park Press, Baltimore, (1981) and the publications cited therein, the entire contents of which being hereby incorporated by reference.

A critical aspect of this invention is the conjugation of the antibody $A^1$ with N,N,N-trimethylammoniumphenyl compounds of the formula:

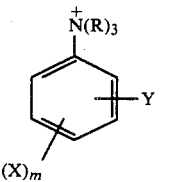

wherein

R, X and m are as defined above with regard to Formula I, and

Y is fluoro, chloro or sulfonyl.

The N,N,N-trimethylammoniumphenyl compound is conjugated to the antibody $A^1$ by allowing the compound to react in a solution containing the antibody. The reaction solution can be aqueous or certain polar, watermiscible organic solvents such as acetone or di-methyl-sulfoxide may be present. The reaction solution has a pH of from 7–11 and preferably from 8–10. Buffering salts such as phosphate, borate, carbonate or organic buffering ions which are not themselves reactive with either reactant may be present.

The time, temperature and amounts of reactants can be varied to achieve a desired degree of substitution. For conjugating with antibodies, from 1 to 350 substituents may be coupled, depending upon the antibody and other factors. With IgG antibodies, for example, the maximum practical degree of substitution is about 70 N,N,N-trimethylammoniumphenyl groups. Preferably from 2 to 40 and optimally from 10 to 20 groups are substituted. With IgM, for example, a larger number of substituents up to 350 groups can be substituted. The N,N,N-trimethylammoniumphenyl substituted antibody can be separated from other reactants by dialysis, molecular sieve chromatography, or ion exchange chromatography.

Novel trimethylammoniumphenyl reagents which are particularly suitable for conjugating with antibodies are described in formula IV

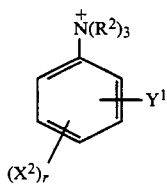

(IV)

wherein
$R^2$ is methyl or ethyl;
$X^2$ is nitro, iodo, bromo, methoxy, carboxy or acetyl;
$Y^1$ is sulfonyl; and
r is 0, 1 or 2.

When X is a nitro group, greater selectivity and sensitivity is achieved in the conjugation of the second antibody with the N,N,N-trimethylammoniumphenyl substituted antibody of Formula I.

The compounds of Formula III and IV can be prepared by procedures known in the art. The 4-chloro-3,5-dinitro-N,N,N-trimethylphenylammonium halides, for example, can be prepared by reaction with dimethylamine in water, the precipitate being methylated according to the procedure of Bevan, et al *J. Chem. Soc.* 238 (1968). The fluoro compounds wherein Y is fluoro such as 4-fluoro-3,5-dinitro-N,N,N-trimethylphenylammonium iodide can be prepared from the corresponding 4-amino compounds by the Sandmeyer reaction. The sulfonyl compounds wherein Y and $Y^1$ are sulfonyl such as a 3,5-dinitro-N,N,N-trimethylammoniumbenzene-4-sulfonic acid halide can be prepared from the corresponding 4-chloro compounds by the procedures of Golumbic et al, *J. Org. Chem.* 11, 518 (1946).

The second critical reagents of this invention are the second antibodies, i.e., antibodies made to selectively bind with the N,N,N-trimethylammoniumphenyl substituted antibodies of Formula I. The binding occurs through the N,N,N-trimethylammoniumphenyl group. These are prepared in immunological response to an antigenic compound of Formula II by conventional procedures and are labeled with a detector label. The antigenic compounds of Formula II are another aspect of this invention.

$A^2$ is preferably different from $A^1$ to minimize cross-reactivity. However, the $A^2$ antibodies can be the same as the $A^1$ antibodies if they have been purified to remove antibodies which bind to the antigenic portion of the hapten-antigen conjugate rather than the hapten portion. This purification can be effected by conventional affinity chromatography of the animal serum containing the antibodies or an antibody fraction obtained therefrom. In this procedure the antibody solution is passed through a column containing the hapten conjugate to an insoluble support such as SEPHAROSE beads (Pharmacia), and the hapten bound antibody is selectively eluted therefrom.

It is within the scope of the present invention to employ antibodies elicited by trimethylammoniumphenyl groups coupled to antigenic materials directly through an amine group or through other coupling linking groups such as the p-azo-N,N,N-trimethylammoniumphenyl compounds previously described by Pressman et al, supra. However, greater selectivity and sensitivity is obtained if the second antibody is prepared by immunological reaction to antigens having N,N,N-trimethylammoniumphenyl group coupled to the antigenic material through an amine group on the antigen. The best results are obtained when the substituents on the N,N,N-trimethylammoniumphenyl group correspond in identity and location to those which are present on the N,N,N-trimethylammoniumphenyl group to which the first antibody is coupled. Superior selectivity and sensitivity are achieved in the preferred embodiments. The preferred second antibody should bind to the substituent N,N,N-trimethylammoniumphenyl group of the first antibody with an affinity constant $K°$, of greater than $10^6$ liters per mole and preferably greater than $10^7$ liters per mole.

The second antibody is labeled with a suitable detector label. Radioactive labels such as $^{125}I$ or other radioactive elements can be applied by procedures known in the art. Techniques for labeling antibodies with iodine-125 ($^{125}I$) or other radioactive labels are well known: Greenwood, Hunter and Glover, *Biochem. J.*, 89:114, (1963). A wide variety of enzymatic labels can be applied, and these are selected in conjunction with the substrate to be used in the analysis by procedures well-known in the art. For example, enzymes such as catalase, peroxidase betaglucouronidase, glucose-6-phosphate dyhydrogenase, urease, phosphatase and glucoseoxidase are conveniently linked to antibodies by art recognized techniques such as those described in U.S. Pat. Nos. 3,875,011, 3,791,932 and 3,879,262, the entire contents of which are hereby incorporated by reference. Fluorescent labels and procedures for coupling them to antibodies are described in U.S. Pat. Nos. 4,256,834 and 4,261,968 *Feltkamp, Immunology* 18, 875 (1970) and U.S. Pat. No. 3,789,116, which are hereby incorporated by reference. For example, fluoroscent labels can be applied by reacting the antibody with a chromogen precursor such as fluorescein isothiocyanate in slightly alkaline aqueous solutions at 4° C. for several hours.

The compounds of Formula I are conjugated with second antibodies in aqueous solutions having a pH of from 2 to 11 at a temperature of from 0° to 50° C. The solutions can also contain conventional buffers, stabilized surfactants and other additives such as are used in standard phosphate buffer solutions (PBS). Incubation times can range from a few minutes in free solution assays up to 10 hours in interactions with a solid substrate.

This invention is further illustrated by the following specific but non-limiting examples. Temperatures are given in degrees centigrade.

EXAMPLE 1

Anti-I-A$^k$ antibody was isolated from isolated from ascites fluid of mice bearing the hybridoma tumor, 10-3.6 by the procedure of Oi, V. et al, *Current Topics in Microb. and Immunol.*, 81, 115 (1978). This antibody binds an antigen found on the surface of B-lymphocytes and some other cell types. Only mice having an allotype I-A$^k$ (or related allotype) within the major histocompatibility (H-2) complex have cells which bind this antibody. Mice of strain CBA/J (H-2$^k$) carry this I-A$^k$ locus marker. Mice of strain Balb/cJ (H-2$^d$) do not.

To 2 mg 10-3.6 antibody in 1 ml phosphate-buffered saline (PBS), 0.2 ml of 0.1M sodium carbonate buffer, pH 9.5 was added, followed by 2 mg 4-fluoro-3-nitro-N,N,N-trimethylammoniumbenzene iodide in 0.2 ml water. The reaction proceeded for 3 hr at 37°. The conjugated antibody was dialyzed exhaustively against PBS. The solution was sterilized by passage through a 0.2 micron filter to yield 2-nitro-4-(N,N,N-trimethylammonium)phenyl substituted antibody.

EXAMPLE 2

Repeating the procedure of Example 1 but replacing the 4-fluoro-3-nitro-N,N,N-trimethylammoniumbenzene iodide with
4-fluoro-N,N,N-trimethylammoniumbenzene iodide;
4-fluoro-2-nitro-N,N,N-trimethylammoniumbenzene iodide;
4-fluoro-3,5-dinitro-N,N,N-trimethylammoniumbenzene iodide;
3-fluoro-4-nitro-N,N,N-trimethylammoniumbenzene iodide;
3-fluoro-N,N,N-trimethylammoniumbenzene iodide;
4-chloro-N,N,N-trimethylammoniumbenzene iodide;
4-chloro-3-nitro-N,N,N-trimethylammoniumbenzene iodide;
4-chloro-2-nitro-N,N,N-trimethylammoniumbenzene iodide;
4-chloro-3,5-dinitro-N,N,N-trimethylammoniumbenzene iodide;
3-chloro-4-nitro-N,N,N-trimethylammoniumbenzene iodide;
N,N,N-trimethylammoniumbenzene-4-sulfonic acid iodide;
3-nitro-N,N,N-trimethylammoniumbenzene-4-sulfonic acid iodide;
2-nitro-N,N,N-trimethylammoniumbenzene-4-sulfonic acid iodide;
3,5-dinitro-N,N,N-trimethylammoniumbenzene-4-sulfonic acid iodide; and
4-nitro-N,N,N-trimethylammoniumbenzene-3-sulfonic acid iodide,
yields the corresponding N,N,N-trimethylammoniumphenyl substituted antibodies.

EXAMPLE 3

Antibodies which specifically couple with the N,N,N-trimethylammoniumphenyl group are isolated from a rabbit immunized with amine group linked 3-nitro-N,N,N-trimethylammoniumphenyl substituted bovine serum albumin by the procedures described by Fenton and Singer *Biochemistry*, 10, 1429–1473 (1971). The antisera is passed over a column of agarose beads to which the N,N,N-trimethylammonium phenyl group has been attached by spacer groups. The spacer groups are attached to the beaded agarose after activation of the agarose with cyanogen bromide in an alkaline pH. The specific antibody is eluted by passage of a solution of N,N,N-trimethylammoniumbenzene chloride over the column. The antibody-containing solution is dialyzed against PBS to free it from hapten. The N,N,N-trimethylammoniumphenyl derivative of the bovine serum albumin is prepared by reacting 4-fluoro-3-nitro-N,N,N-trimethylammoniumbenzene iodide with BSA at pH 7.4, and dialyzing the product solution exhaustively against phosphate-buffered saline (PBS).

EXAMPLE 4

Repeating the procedure for Example 3 but replacing the 4-fluoro-3-nitro-N,N,N-trimethylammoniumbenzene iodide with
4-fluoro-N,N,N-trimethylammoniumbenzene iodide;
3-fluoro-4-nitro-N,N,N-trimethylammoniumbenzene iodide;
4-fluoro-3,5-dinitro-N,N,N-trimethylammoniumbenzene iodide;
3-fluoro-4-nitro-N,N,N-trimethylammoniumbenzene iodide;
4-chloro-N,N,N-trimethylammoniumbenzene iodide;
4-chloro-3-nitro-N,N,N-trimethylammoniumbenzene iodide;
3-chloro-4-nitro-N,N,N-trimethylammoniumbenzene iodide;
4-chloro-3,5-dinitro-N,N,N-trimethylammoniumbenzene iodide;
3-chloro-4-nitro-N,N,N-trimethylammoniumbenzene iodide;
N,N,N-trimethylammoniumbenzene-4-sulfonic acid iodide;
3-nitro-N,N,N-trimethylammoniumbenzene-4-sulfonic acid iodide;
2-nitro-N,N,N-trimethylammoniumbenzene-4-sulfonic acid iodide;
3,5-dinitro-N,N,N-trimethylammoniumbenzene-4-sulfonic acid iodide; and
4-nitro-N,N,N-trimethylammoniumbenzene-3-sulfonic acid iodide,
yields the corresponding labeled bovine serum albumin antigenic compounds.

Immunizing rabbits with the above obtained antigenic materials yields antibodies which bind specifically with N,N,N-trimethylammoniumphenyl substituted antibodies.

EXAMPLE 5

To 0.34 mg fluorescein isothiocyanate placed as a dry solid in a screw-capped test tube was added 64 micrograms of N,N,N-trimethylammoniumbenzene iodide in 25 microliters of water, 0.2 ml 1M sodium carbonate buffer, pH 9.5, and 17 mg of the antibody product obtained in Example 3 in 2 ml PBS. The reaction was continued for six hours on ice, after which the solution was dialyzed against 0.015M NaCl, 0.01M sodium phosphate. This solution was applied to a DEAE-cellulose column equilibrated in the same buffer. Step-wise increases in NaCl concentration gave fractions eluting between 0.05M NaCl and 0.15M NaCl which were pooled and dialyzed against PBS. The solution was sterilized by passage through a 0.2 micron filter to yield a fluorescein labeled antibody.

EXAMPLE 6

The antibody from Example 3 is labeled with horse radish peroxidase (HRPO) according to the method of Nakane and Kawaoi, *J. of Histochem. and Cytochem.* 22, 1084–1091, (1974). Five mg HRPO in 1 ml 0.3M NaHCO$_3$ is added to 0.1 ml of 1 wt.% 1-fluoro-2,4-dinitrobenzene in ethanol. After 1 hr at RT, 1 ml of 0.04M NaIO$_4$ in water is added. After 30 min, 1 ml of 0.16M ethylene glycol in water is added. The solution is allowed to stand for 1 hr, and then is dialyzed against three 1-liter changes of 0.01M sodium carbonate buffer, pH 9.5, at 4°. Five mg of antibody in 0.5 ml buffer is added to the HRPO solution and allowed to stand at RT for 3 hr. The solution is chilled to 4°, and 5 mg NaBH$_4$ is added with stirring. The solution is allowed to stand for 3 hr, and then is dialyzed against PBS. Passage of this solution over G-200 SEPHADEX (Pharmacia) equilibrated and eluted with PBS yields HRPO-labeled antibody as the first peak. This solution is diluted to a concentration of 1 wt % in BSA and sterilized by passage through a 0.2 micron filter.

EXAMPLE 7

Antibody from Example 3 is made radioactive by adding to 0.1 mg antibody in 0.05 ml 0.1M sodium bicarbonate, 0.3 mc Na $^{125}$I in 0.01 ml water, followed by 0.015 mg chloramine T in 0.01 ml water. After incubating for 1.5 min., the reaction is stopped by the addition of 0.015 mg Na$_2$S$_2$O$_5$ in 0.01 ml water. After 1 min., 1 mg BSA is added in 0.1 ml PBS. This solution is passed over a column of 0.5 ml Dowex-1 (Dow Chemical Co.) and eluted with 2 ml of 1% BSA in PBS. The $^{125}$I-antibody solution is stored frozen.

EXAMPLE 9

Single-cell suspensions of CBA/J or Balb/cJ splenocytes were prepared in Hank's Balanced Salt Solution, 5% in fetal bovine sera (FBS). This solution was used for dilution of reagents and washing of cells. All procedures were performed at 4° or on ice. Portions of one or the other suspension were distributed into 3 ml conical test tubes and centrifuged at 400 g for 5 min. The resulting pellets were resuspended in two drops containing about 0.4 micrograms NTMA-conjugated 10-3.6 antibody, or diluent alone, and left for 20 min. The suspension was diluted to 2 ml and centrifuged. The resulting pellet was resuspended in 2 ml of diluent and centrifuged again, twice. The washed cells were resuspended in 2 drops of solution of fluorescein-labeled antibody obtained in Example 5 containing about 4 micrograms of antibody. Incubation and washing procedures were repeated, except that the last pellet was centrifuged through 0.2 ml FBS underlaying the cell suspension. The supernatant was removed, and the pellet resuspended by tapping the tube. This cell suspension was smeared on glass slides, air dried, and fixed in ethanol. The slides were mounted and the frequency of fluorescent cells was determined by examination under a microscope (Zeiss Universal) equipped for this purpose.

Among CBA/J splenocytes treated with both antibodies, 43% were judged positive (140/325). A fourfold increase in concentration of the first antibody or a fivefold decrease in concentration of the second antibody did not appreciably alter the result (129/372 and 127/294), although in the latter case, staining was judged dull. Omission of the first antibody resulted in cells judged negative for staining. Balb/cJ splenocytes were judged negative for staining at all concentrations of first and second antibody used to stain CBA/J splenocytes.

EXAMPLE 9

Assay of Anti-Insulin Antibodies in Human Serum using a sandwich assay.

(a) Preparation of insulin-coated polystyrene tubes. One ml of a 1 mg/l solution of porcine or bovine insulin in 0.01M sodium phosphate buffer, pH 8.0, is placed in a 10×75 mm polystyrene test tube. These are incubated together overnight at 4°. The contents of the tube are removed, and the tube washed with saline and incubated with 0.2% TWEEN 20 (Atlas Chem. Ind., Inc.) in saline, 1 hr at RT. The tube is washed as before and used in the following procedure.

(b) Isolation of anti-insulin antibodies. The globulin fraction of sera from diabetic patients is passed over a column of agarose beads to which porcine insulin has been covalently attached. The absorbed sera is then passed over a similar column, to which bovine insulin is attached. Both columns are washed with saline and bound antibodies eluted with 0.01M HCl in saline. The acid eluates are neutralized, concentrated to 2 mg/ml, and sterilized for storage.

(c) Preparation of pure anti-HGG antibodies coupled to 3-nitrophenyltrimethylammonium. Sera from rabbits immunized with HGG are treated as in (b) above by passage over a column of HGG-agarose beads. The NTMA-conjugate of purified antibodies are prepared as described in Example 1.

(d) Sera from patients suspected of bearing anti-insulin antibodies are twice diluted tenfold in 1% HSA in phosphate-buffered saline. One ml of diluted sera is added to the insulin-coated tubes, and left for 1 hr at 37°. The contents of the tube are discarded, and the tube washed with saline. Hapten-conjugated anti-HGG, diluted in 1% HSA solution in saline, is then added. Incubation and washing are repeated. The HRPO-conjugated anti-hapten antibody in Example 6, diluted as above, is incubated with the tube for 1 hr, and the tube is washed as before. The tube is then washed once with 0.1M citrate buffer, pH 6.0, before adding 1 ml of 0.1M citrate buffer, pH 6.0, containing 1 mg/ml o-phenylenediamine hydrochloride and 0.015% hydrogen peroxide. After 1 hr, the reaction is stopped by addition of 1 ml 2M sulfuric acid. Absorbance of the solution at 492 nm is measured. By comparison to a standard curve prepared by substituting dilutions of purified anti-insulin antibody, the amount of anti-insulin antibody in patient's serum can be identified.

EXAMPLE 10

Competitive Assay for Insulin using hapten-conjugated insulin.

(a) Immobilization of guinea pig anti-insulin globulin. The globulin fraction of guinea pig anti-porcine insulin from sera is taken by ammonium sulfate precipitation. Polystyrene test tubes are coated with this globulin fraction, diluted in carbonate buffer, 0.05M, pH 9.5, by incubation overnight at 4°. The dilution is chosen so that maximal binding of insulin is in the range of interest. The antibody solution is removed, washed with saline, and incubated with 0.2% TWEEN 20 in saline. After 1 hr at room temperature, the tube is again washed with saline.

(b) (N-alpha-3-nitrophenyltrimethylammoniumglycyl$^{41}$)-insulin is prepared according to Easter and Drewes (1979), by reacting the hapten with porcine insulin in aqueous media at pH 8.0 for 3 hr at 40°, in the presence of zinc. The product is isolated by chromatography on DEAE-cellulose in the presence of urea.

(c) Horseradish peroxidase-conjugated anti-phenyltrimethylammonium antibodies are prepared as described in Example 6.

(d) A hapten-substituted insulin solution is placed in the anti-insulin antibody coated test tube, together with various concentrations of insulin, all diluted in 1% HSA in PBS. The tube is left for 1 hr at 37°, the contents removed, and the tube is washed. The enzyme conjugated anti-hapten in (c), diluted in the same buffer, is added to the tube, and left for 1 hr at 37°. The tube is washed and the enzyme reaction observed as described in Example 9. Decreasing amounts of enzyme activity are given by increasing amounts of unlabeled insulin. By comparing the amount of inhibition given by solutions containing unknown amounts of insulin to the curve thus generated, the amount of insulin in the unknown solution can be determined.

The invention claimed is:

1. A sandwich immunoassay method comprising coupling an N,N,N-trimethylammoniumphenyl substituted antibody of the formula:

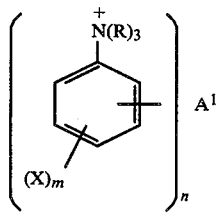 (I)

wherein
  $A^1$ is an antibody bonded through an amino linkage thereof;
  R is methyl or ethyl;
  X is nitro, iodo, bromo, methoxy, carboxy or acetyl;
  m is 0, 1 or 2; and
  n is from 1 to 350;
with labeled antibody prepared in immunological response in a mammal to antigenic compound of the formula:

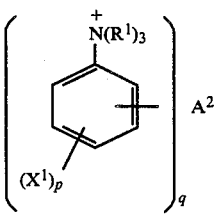 (II)

wherein
  $A^2$ is an antigen;
  $R^1$ is methyl or ethyl;
  $X^1$ is nitro, iodo, bromo, methoxy, carboxy or acetyl;
  p is 0, 1 or 2; and
  q is from 1 to 350.

2. The method of claim 1 wherein R, X, and m are the same as $R^1$, $X^1$ and p, respectively.

3. The sandwich immunoassay method of claim 1 wherein the compound of Formula I is 2-nitro-4-(N,N,N-trimethylammonium)phenyl substituted antibody.

4. The sandwich immunoassay method of claim 3 wherein the antigenic compound of Formula II is 2-nitro-4-(N,N,N-trimethylammonium)phenyl substituted bovine serum albumin conjugated through amine groups of the bovine serum albumin.

5. A N,N,N-trimethylammoniumphenyl substituted antibody of the formula:

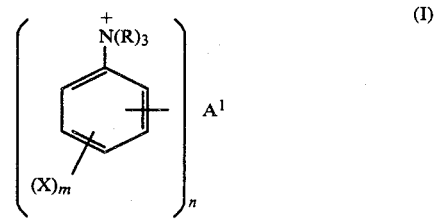 (I)

wherein
  $A^1$ is an antibody bonded through an amino linkage thereof;
  R is methyl or ethyl;
  X is nitro, iodo, bromo, methoxy, carboxy or acetyl;
  m is 0, 1 or 2; and
  n is from 1 to 350.

6. As an antibody compound of claim 5, 2-nitro-4-(N,N,N-trimethylammonium)phenyl substituted antibody.

7. An antibody prepared in immunological response in a mammal to a compound of the formula:

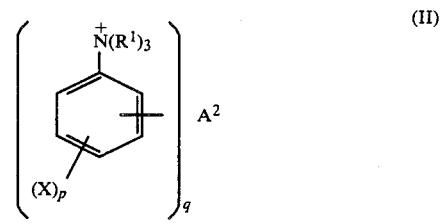 (II)

wherein
  $A^2$ is an antigen bonded through an amino linkage thereof;
  $R^1$ is methyl or ethyl;
  $X^1$ is nitro, iodo, bromo, methoxy, carboxy or acetyl;
  p is 0, 1 or 2; and
  q is from 1 to 350;
which specifically binds with compounds of claim 5.

8. An antibody of claim 7 prepared in immunological response to 2-nitro-4-(N,N,N-trimethylammonium)phenyl substituted bovine serum albumin.

9. The antibody of claim 7 having a detector label selected from the group of radioactive, enzymatic and fluorescent labels.

10. A N,N,N-trimethylammoniumbenzene compound of the formula:

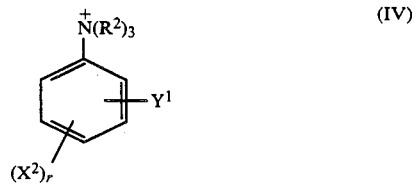 (IV)

wherein
  $R^2$ is methyl or ethyl;
  $X^2$ is nitro, iodo, bromo, methoxy, carboxy or acetyl;

$Y^1$ is sulfonyl; and
r is 0, 1 or 2.
11. An antigenic compound of the formula:
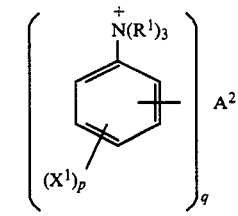
wherein
- $A^2$ is an antigen bonded through an amino linkage thereof;
- $R^1$ is methyl or ethyl;
- $X^1$ is nitro, iodo, bromo, methoxy, carboxy or acetyl;
- p is 0, 1 or 2; and
- q is from 1 to 350;
with the proviso that when $X^1$ is nitro, $A^2$ is not insulin.
* * * * *